(12) United States Patent
Ben-Arie (10) Patent No.: US 9,949,864 B2
(45) Date of Patent: *Apr. 24, 2018

(54) WASHABLE OSTOMY POUCH III

(71) Applicant: Jezekiel Ben-Arie, Chicago, IL (US)

(72) Inventor: Jezekiel Ben-Arie, Chicago, IL (US)

(*) Notice: Subject to any disclaimer, the term of this patent is extended or adjusted under 35 U.S.C. 154(b) by 351 days.

This patent is subject to a terminal disclaimer.

(21) Appl. No.: 14/536,700

(22) Filed: Nov. 10, 2014

(65) Prior Publication Data
US 2015/0065970 A1 Mar. 5, 2015

Related U.S. Application Data

(66) Continuation-in-part of application No. 14/304,909, filed on Jun. 14, 2014, Substitute for application No. 62/060,026, filed on Oct. 6, 2014.

(60) Provisional application No. 61/838,230, filed on Jun. 22, 2013.

(51) Int. Cl.
| A61F 5/442 | (2006.01) |
| A61F 5/44 | (2006.01) |
| A61F 5/441 | (2006.01) |
| A61F 5/445 | (2006.01) |
| A61F 5/443 | (2006.01) |

(52) U.S. Cl.
CPC .............. *A61F 5/442* (2013.01); *A61F 5/441* (2013.01); *A61F 5/443* (2013.01); *A61F 5/445* (2013.01); *A61F 5/4405* (2013.01); *A61F 5/4407* (2013.01)

(58) Field of Classification Search
CPC combination set(s) only.
See application file for complete search history.

(56) References Cited

U.S. PATENT DOCUMENTS

| 2,520,831 | A | * | 8/1950 | Chincholl | A61F 5/445 604/335 |
| 2,782,785 | A | * | 2/1957 | Arcand | A61F 5/445 604/334 |
| 3,690,320 | A | * | 9/1972 | Riely | A61F 5/4407 604/333 |
| 3,815,794 | A | * | 6/1974 | Carlisle | B65D 75/5822 222/107 |
| 3,865,109 | A | * | 2/1975 | Elmore | A61F 5/441 604/339 |
| 3,897,780 | A | * | 8/1975 | Trousil | A61F 5/445 604/344 |

(Continued)

*Primary Examiner* — Todd J Scherbel
*Assistant Examiner* — Guy K Townsend (57) ABSTRACT

A washable ostomy pouch which enables accumulating discharged waste and also to drain and wash it without detaching the pouch from the user. The washable pouch has an abdominal inlet coupling, a draining outlet and a washing inlet. The washable pouch has a flat structure constructed of two planar sheets of flexible material, which are fused together at their margins all along their borders except for inlet and outlet openings. Both the washing inlet and draining outlet have seals. The washing inlet's funnel shape facilitates pouring water into the pouch, whereby liquefying the discharged waste and enabling easier draining. The abdominal adhesive faceplate is attached to the washable pouch on its distal side. The abdominal adhesive faceplate which has on its proximal side an adhesive layer of skin barrier surrounding a central opening enables to adhere the abdominal adhesive faceplate to the user's abdominal skin surrounding the user's stoma.

9 Claims, 7 Drawing Sheets

(56) References Cited

U.S. PATENT DOCUMENTS

| | | | | |
|---|---|---|---|---|
| 4,233,977 A * | 11/1980 | Mattson | | A61F 5/4407 604/335 |
| 4,372,308 A * | 2/1983 | Steer | | A61F 5/441 604/333 |
| 4,403,991 A * | 9/1983 | Hill | | A61F 5/443 604/337 |
| 4,465,486 A * | 8/1984 | Hill | | A61F 5/443 24/30.5 R |
| 4,654,037 A | 3/1987 | Fenton | | |
| 4,692,159 A | 8/1987 | Kuzemchak | | |
| 4,755,177 A * | 7/1988 | Hill | | A61F 5/443 604/336 |
| 4,863,447 A * | 9/1989 | Smith | | A61F 5/441 251/323 |
| 4,941,878 A | 7/1990 | Petrik | | |
| 5,037,408 A * | 8/1991 | Henry | | A61F 5/445 604/332 |
| 5,470,325 A | 11/1995 | Fundock | | |
| 5,503,633 A | 2/1996 | Saunders | | |
| 5,941,640 A * | 8/1999 | Thatcher | | A45F 3/20 383/22 |
| 6,171,288 B1 * | 1/2001 | Wiltshire | | A61F 5/441 604/333 |
| 6,224,581 B1 | 1/2001 | Withers | | |
| 6,267,506 B1 * | 7/2001 | Campion | | A45C 11/22 224/148.2 |
| 6,336,918 B1 * | 1/2002 | Olsen | | A61F 5/4407 604/332 |
| 6,582,410 B1 | 6/2003 | Rutman | | |
| 6,644,854 B2 * | 11/2003 | Lien | | A45F 3/20 222/175 |
| D501,399 S * | 2/2005 | Tobolka | | A61F 5/44 D9/434 |
| 6,918,898 B2 | 7/2005 | King | | |
| D607,559 S * | 1/2010 | Schena | | A61F 5/44 D24/118 |
| D618,791 S * | 6/2010 | Schena | | A61F 5/44 D24/118 |
| 7,879,015 B2 * | 2/2011 | Villefrance | | A61F 5/4405 604/332 |
| 7,879,016 B2 * | 2/2011 | Mandzij | | A61F 5/4407 4/144.1 |
| 7,918,836 B2 | 5/2011 | Gill | | |
| 8,016,802 B1 | 9/2011 | Schena | | |
| 8,167,857 B2 | 1/2012 | James | | |
| 2004/0052437 A1 * | 3/2004 | Tobolka | | B65D 75/008 383/104 |
| 2006/0079854 A1 * | 4/2006 | Kay | | A61F 5/4405 604/328 |
| 2006/0106354 A1 | 5/2006 | Vantroostenberge | | |
| 2006/0111682 A1 * | 5/2006 | Schena | | A61F 5/4407 604/334 |
| 2006/0155252 A1 | 7/2006 | Walker | | |
| 2006/0253090 A1 * | 11/2006 | Bradley | | A61F 5/4405 604/334 |
| 2008/0060679 A1 | 3/2008 | Rosenberg | | |
| 2009/0163885 A1 | 6/2009 | Pedersen | | |
| 2015/0018789 A1 * | 1/2015 | Ben-Arie | | A61F 5/442 604/334 |
| 2015/0065970 A1 * | 3/2015 | Ben-Arie | | A61F 5/442 604/333 |

* cited by examiner

WASHABLE OSTOMY POUCH III

CROSS-REFERENCE TO RELATED APPLICATIONS

This Application is Continuation In Part of application Ser. No. 14/304,909 Filed on Jun. 14, 2014
This Application claims the benefit of a Provisional Patent Applications:
Ser. No. 61/838,230 filed on 22 Jun. 2013 (via Continuation In Part of application Ser. No. 14/304,909 Filed on Jun. 14, 2014)
Ser. No. 62/060,026 filed on 6 Oct. 2014

FEDERALLY SPONSORED RESEARCH

Not Applicable

SEQUENCE LISTING OR PROGRAM

Not Applicable

BACKGROUND OF THE INVENTION

1. Field of the Invention

The invention is in the area of ostomy pouches.

2. The Problems in Draining Ostomy Pouches

Drainable pouches are being used by people who underwent ileostomy also referred to as ostomy. Ostomy is the construction of an artificial opening from the ileum through the abdominal wall, permitting drainage of the contents of the small intestine. The drainable pouch is attached to the abdominal opening and collects the discharged waste drained from the small intestine. Every few hours the pouch is filled and needs to be drained. Usually these pouches have the shape of a bag and are made of flexible material such as plastic sheets. The pouch's inlet is attached to the abdominal opening (also called stoma) usually by an abdominal inlet coupling which can detachably secure the washable pouch to an abdominal adhesive faceplate. The abdominal adhesive faceplate has on its proximal side an adhesive layer called skin barrier surrounding a central opening. The adhesive layer of skin barrier enables to adhere said abdominal adhesive faceplate to the user's abdominal skin surrounding the user's stoma. There is a second type of drainable pouches which have an abdominal inlet which is connected directly to the abdominal adhesive faceplate without a detachable coupling.

Prevalent pouches also have an outlet from which the pouch is being drained. This outlet is sealed during discharged waste accumulation and can be opened for drainage and re-sealed afterwards. When the user drains the pouch, the user has to open the outlet and to squeeze the pouch in order to drain it. The inventor personally had ileostomy and had been using these pouches for few years. Users of ostomy pouches are experiencing a major difficulty in the draining process. Since the discharged waste is highly viscous and sticky, it adheres to the inner walls of the pouch and draining it requires a lot of squeezing. Even after a lot of squeezing the pouch is not completely emptied and remains with considerable residue inside. To alleviate this problem, the inventor developed a washing and draining procedure in which the user is adding water to the pouch through the draining outlet. Next, the user mixes the discharged waste with the water into a fluent mixture and then drains the mixture via the outlet. This process needs repeating 2-3 times until the pouch is entirely cleaned. It was found that this washing procedure is faster, easier, more hygienic and achieves much better drainage. Notice that the whole procedure does not require detaching the pouch from the stoma.

3. Prior Art

Searching the PTO database for inventions which employ various means for washing pouches yielded several patents and patent applications. But all of them were entirely dissimilar to our invention. Several patent applications propose various methods for flushing ostomy pouches. In US 20080060679 Rosenberg proposes to use a special flushing water container which connects to the pouch's outlet. Rosenberg claims no water spills but since the outlet is located at the bottom of the pouch, it presents a major problem how to disconnect the container without spilling. In addition, this arrangement requires special installation in every toilet used.

In U.S. Pat. No. 4,692,159 Kuzemchak invents a flushing nozzle which fits the pouch's inlet and which connects to a water pipe. However, it seems that Kuzemchak forgot that this inlet is connected to the user's abdominal opening and removing the pouch when it is filled with discharged waste is almost impossible without spilling. Very similar approaches are presented in U.S. Pat. No. 6,224,581 by Withers et al. and in US 20060155152 by Walker.

In U.S. Pat. No. 6,582,410 Rutman invents an ostomy drainage apparatus which consists of a tube which connects the pouch's outlet to a large container. We fail to see how this is better than simply draining the pouch directly to a toilet bowl.

In U.S. Pat. No. 4,941,878 Petrik invented an ostomy pouch flasher which is basically a metal pipe with few holes at its end and a water pipe inlet at its other end. This pipe is designed to be inserted into the pouch and help flushing it.

In US 2006/0106354 A1 Vantrustenberge invents an ostomy pouch with 3 openings. The first one serves as an inlet which is connected to the user's abdominal opening (stoma). The second one is a wide pouch outlet which is used for pouch draining. The third opening in the pouch is a port connected to a one way valve which has a stem pipe at the valve's outlet. The third opening has two uses. The first use is for expelling gases accumulated in the pouch wherein the valve is activated by pressing the pouch and creating enough pressure which opens the one directional valve and allowing the gas to exit. The second use of the third opening is to use it for flushing the bag after draining. The stem pipe is connected to a water source and water is being forced into the pouch. This invention has two major flaws. The first one is the need for a pressurized water source that needs to be connected to the stem pipe for flushing. The second problem is a contradiction in the invention design because if the one way valve is designed to expell gasses from the pouch outwards it will block any flow of rinsing water inwards into the pouch. A similar invention is presented by King in U.S. Pat. No. 6,918,898 B2. King uses an enema bag as an irrigation water source which is connected by a tube to a plapped opening in the pouch. In our opinion, enema's dripping is much too slow for pouch rinsing and a flapped input will allow linkage of gasses and waste from the pouch.

Schena in U.S. Pat. No. 8,016,802 B1 invented a pouch irrigator which consists of a curved porous pipe (called manifold by the inventor) installed inside the pouch. Schena is manufacturing his invention under the name EZ-Clean.

The irrigator has a pipe inlet installed at a pouch's opening. This invention is not practical because it requires a pressurized water source connected to the irrigator's inlet. Thus, the user can use Schena's invention only in toilets with appropriate water source. It is also very expensive solution for a disposable pouch because the manifold needs to be disposed with the pouch every few days. Another disadvantage of Schena's pouch is that it is quite bulky under the clothes. A similar pouch irrigator composed of a porous pipe installed inside the pouch was invented by Fenton in U.S. Pat. No. 4,654,037. Similar invention with pipe irrigation is in U.S. Pat. No. 7,918,836 B2 by Gill et al.

An ostomy suction system was invented by James in U.S. Pat. No. 8,167,857 B2, which uses vacuum tube connected to the pouch outlet for efficient draining. Fundock in U.S. Pat. No. 5,470,325 invented an irrigation and venting assembly which is composed of a simple pipe inlet installed on the top of the pouch. The pipe inlet needs to be connected to pipe which is attached to a water source for rinsing.

An ostomy bag cleaning apparatus is described in U.S. Pat. No. 5,503,633 by Saunders. The apparatus is actually a drainage construction which enables to flush used ostomy pouches with a water sprinkler over the toilet. Similar approach to pouch cleaning is in US 2006/0237039 A1 by Sarvis. An peelable ostomy bag which can be cleaned by peeling it from the abdominal opening is invented by Pedersen et al. in US 2009/0163885 A1.

BRIEF SUMMARY OF THE INVENTION

The present invention pertains to an ostomy appliance with novel pouch structure which enables easy washing and draining of ostomy pouches without detaching the pouch from the user. Conventional ostomy pouches are made of flexible material such as plastic and have an inlet opening which is attached to the abdominal opening of the user. The pouch accumulates the discharged waste excreted from the abdominal opening (called stoma). Every few hours the pouch is filled and needs to be drained. Conventional pouches have an outlet at their bottom from which the pouch is being drained. This outlet is sealed most of the time when discharged waste is being accumulated and can be opened for drainage and re-sealed afterwards. When the user drains the pouch, the user has to open the outlet and to squeeze the pouch in order to force out the discharged waste. Users are experiencing a major difficulty in such draining process since the discharged waste is highly viscous and sticks to the pouch walls. Thus, large portions of the discharged waste still remain in the pouch even after a lot of squeezing. Few inventions (described in the prior art section) propose to improve the drainage by mixing the discharged waste with water, which converts it to more fluent mixture that can be easily drained. These inventions propose to add water to the pouch via various structures of pipe inlets installed in the pouch. There are two major problems with these approaches which renders them impractical. Firstly, pipe inlets need to be connected to a water source via a flexible pipe. This requirement limits the usage of such pouches only to special toilets with a water source and fitting pipes. Since most toilets are not equipped with such water sources, users of pouches with pipe inlet can use them only in few locations. Recently, EZ-Clean company proposed a flexible bottle which is attached to the pipe inlet of their pouch—as a water source. However, it is only a partial solution because it requires the user to carry a flexible bottle with connecting pipe. Even more serious problem arises from the requirement to include in each pouch an inner pipe with a pipe inlet. Adding a pipe structure to each pouch makes it quite bulky and expensive since ostomy pouches need to be replaced with new ones every few days.

Our invention proposes an economical and efficient solution to draining and washing pouches by adding an additional washing inlet opening at the top of the central cavity which accumulates the waste in the pouch. The washing inlet is fluidly connected to a lower washing duct opening of an elongated washing duct. The washing duct is made of a washing duct wall (i.e. a tubular wall which is not necessarily cylindrical) which has a washing duct seal on its upper side. The washing duct seal enables to seal the upper washing duct opening. Usually the upper washing duct opening is sealed and it is opened when the user wants to pour water into the central cavity in order to wash the pouch. The central cavity has also a draining outlet opening at the bottom of the central cavity. The draining outlet is fluidly connected to an upper draining duct opening of an elongated draining duct. The draining duct is made of a draining duct wall (i.e. a tubular wall which is not necessarily cylindrical) which has a draining duct seal on its lower side. The draining duct seal enables to seal the lower draining duct opening. Usually the lower draining duct opening is sealed and it is opened when the user wants to drain the central cavity.

The washable pouch structure can be quite economically manufactured because both the washing and the draining ducts are made from the same flexible flat sheets as the rest of the washable pouch including the washing and draining duct seals. The invention also enables efficient drainage and washing because it does not require any special water source and the washing duct which has a funnel shape can be filled from a variety of water vessels and containers. Since the proposed washing duct is located at the top of the washable pouch and the draining duct is located at the bottom of the washable pouch, the washing and rinsing process is quite efficient. Placing the upper washing duct opening at elevated location prevents accumulated waste overflow. To facilitate water input, the upper washing duct opening has a shape of a funnel. It is also equipped with a washing duct seal to prevent accidental leakage and odors from the upper washing duct opening.

The washing duct could also enable easy expulsion of gases usually excreted from the discharged waste and accumulated in the upper part of the pouch. To get rid of these gasses all the user needs to do is to momentarily open the washing duct seal and let the gasses evaporate.

Another advantage of the washable pouch described in this application is its very flat structure which is relatively cheap to manufacture. The pouch including the washing duct, the abdominal inlet and the draining duct is manufactured by fusing two walls made of flat sheets of flexible material which are fused at their margins all around their outer boundaries (perimeters) except for openings for the washing duct and the draining duct. The walls have identical two dimensional shapes except for an opening in the rear wall for the abdominal inlet. The two dimensional shapes of the front wall and the rear wall include a central area configured for the pouch central cavity and two protruding extensions which extend from the central area for constructing two protruding ducts: the upper one for the washing duct and the lower one for draining duct. The two protruding extensions (ducts) are fluidly connected to the central cavity. The walls are fused at their margins all along their perimeters and the only places the walls are not fused are short perimeter segments located at the openings necessary for the upper washing duct opening and the lower draining duct opening. The pouch's flat structure is not conspicuous when the user wears the pouch under the user's clothes. Other inventions which employ various configurations of rinsing pipes are much more bulky and expensive in manufacturing. Our invention has a wide funnel shaped washing duct which enables the user to rinse the washable pouch using a variety of water sources. Our washing duct also has a washing duct seal which enables to seal the washing inlet when not in use. Expulsion of excess gases from the washable pouch can also be achieved simply by momentarily opening the washing duct seal and sealing it afterwards. Installing a washing duct on top has additional advantages. In our embodiment, we propose to install on the washing duct wall of the washing duct an air filter that enables to remove excess gasses discharged from the solid waste. Usually such filters are installed at the upper side of central cavities of other pouches, but such filters are not separated enough from the waste and become clogged with solid waste even after a very short use. Such clogging effectively blocks the filter and renders it useless. Installing a filter on the washing duct wall of the washing duct separates it more effectively from the solid waste in the pouch because the washing duct extends from the very top of the washable pouch. Other problems that are routinely encountered by users of ostomy pouches are skin wounds and irritation, which are caused by the sharp edges of the adhesive layer of skin barrier which adheres the pouch's abdominal inlet to the user's abdominal skin around the abdominal opening (stoma). For some reason, this adhesive layer of skin barrier, which comprises of a disc made of adhesive material, has sharp edges on its circumference. The user could have avoided many irritations and wounds if these sharp edges would have been tapered or rounded. For this reason, we propose in our embodiment to taper the edges on the circumference (i.e. the perimeter) of the adhesive disc. In summation, our invention is entirely different from all the inventions described above because our invention does not have a valve or a pipe input. Our invention is the only one which has a wide funnel shaped washing duct which enables to rinse the pouch manually using water from any container, bottle or pitcher.

BRIEF DESCRIPTION OF THE DRAWINGS

FIGS. 1 to 7 describe a feasible embodiment of the washable pouch. FIG. 1 also displays the rear flexible wall 1F in which the adhesive abdominal inlet coupling is installed at the rear wall's abdominal inlet opening.

DETAILED DESCRIPTION OF THE DRAWINGS

Figure 1:
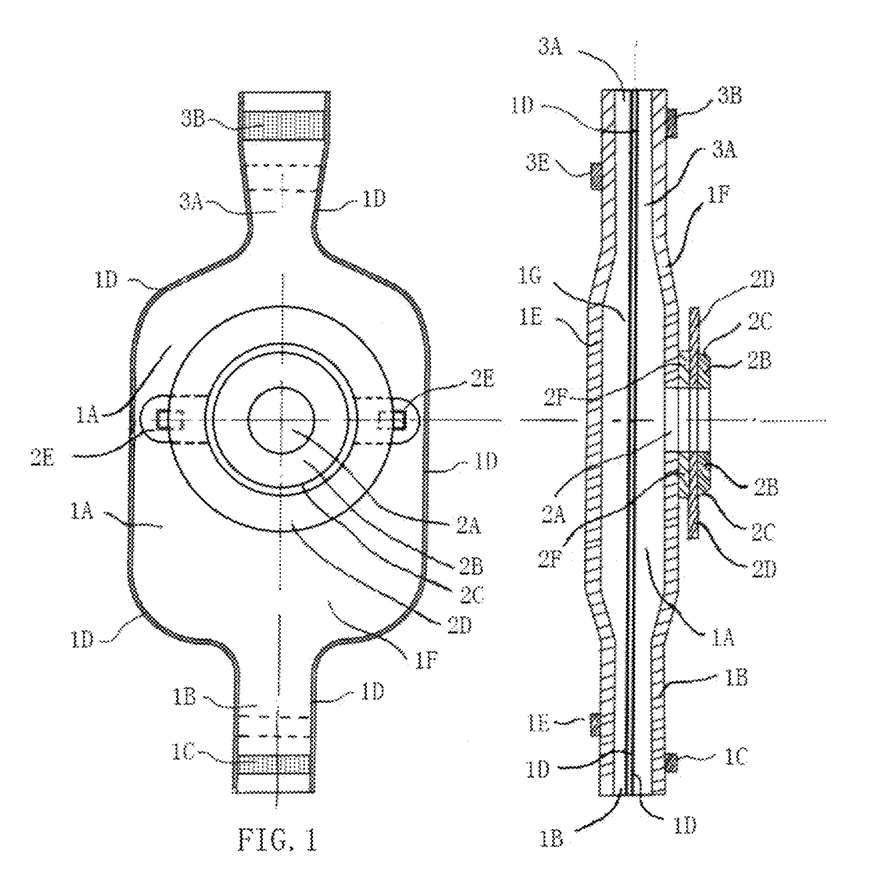
FIG. 1 describes the rear view of the washable pouch 1A and a cross section of the pouch's side view. This includes a front and side view of the abdominal inlet coupling parts 2A, 2B, 2C, 2D which are used to attach the washable pouch to the user's abdominal skin surrounding the user's stoma.

FIG. 1 describes a rear view of an embodiment of the washable pouch 1A. The rear wall 1F which is made of a flexible sheet is illustrated with the abdominal inlet coupling, which includes the abdominal inlet opening 2A which fits the face plate central opening 2A, the adhesive layer of skin barrier 2B with its circumference tapering 2C and the adhesive tape 2D which surrounds the adhesive layer of skin barrier 2B. The parts 2A, 2B and 2D are attached to the faceplate 2F which is seen only in the cross sectional drawing in FIG. 1. The distal side of the abdominal adhesive faceplate 2F is attached to the rear wall 1F. The proximal side of the abdominal adhesive faceplate 2F is attached to the adhesive tape ring 2D and to the adhesive layer of skin barrier 2B. FIG. 1 also shows the draining duct 1B with its interlocking type strip 1C which can be attached to another interlocking type strip 1E by folding the draining duct 1B when one wants to close the draining duct seal. FIG. 1 also describes the washing duct 3A installed at the top of the washable pouch 1A, with its interlocking type strip 3B which can be attached to another interlocking type strip 3E by folding the washing duct 3A when one wants to close the washing duct seal. The washing duct 3A has a shape of a funnel which facilitates pouring water into the washable pouch 1A.

As illustrated in FIG. 1, the rear wall 1F is fused to the front wall 1E all along its perimeter margins 1D except for two short perimeter segments for the upper washing duct opening and the lower draining duct opening. The fused strip 1D is shown as a wide hashed line. The walls 1E and 1F have an identical two dimensional shapes except for the abdominal inlet opening 2A in the rear wall 1F. The central area of the two dimensional shapes 1E and 1F is connected to two protruding extensions which construct the two protruding ducts 1B and 3A for the draining duct 1B and the washing duct 3A respectively. The side view cross section in FIG. 1 shows that the central area of the pouch has a central cavity 1G which is formed between the two walls 1E and 1F (the front 1E and the rear 1F walls respectively). The central cavity 1G provides the washable pouch with a space for discharged waste accumulation.

As depicted in FIG. 1, the faceplate 2F has a shape of a disk. The faceplate 2F has on its proximal side (body side) an adhesive layer of skin barrier 2B surrounding a faceplate central opening 2A which is fluidly connected to the abdominal inlet opening surrounding the stoma. The adhesive layer of skin barrier 2B is designed to adhere to the user's abdominal skin around the stoma. The adhesive layer of skin barrier 2B has a tapered circumference (perimeter) 2C designed to reduce abdominal skin irritation which could have been caused by sharp edges of the adhesive layer of skin barrier 2B. A flexible circular strip of adhesive tape ring 2D is attached to the circumference of the faceplate 2F. The adhesive tape ring 2D is designed to adhere the faceplate circumference to the abdominal skin and to strengthen the faceplate adherence provided by the adhesive layer of skin barrier 2B, which adheres to the user's abdominal skin surrounding the user's stoma.

FIG. 1 depicts both the draining duct seal and the washing duct seal in open positions. The cross section drawing in FIG. 1 also shows a cross section of the rear wall 1E, the pouch's central cavity 1G and the fusing region 1D. The fusing region 1D is shown more clearly in the frontal drawing of FIG. 1 on the left, in which it is illustrated as a thick black line 1D which covers the whole perimeter of the washable pouch except for the openings for the draining duct 1B and for the washing duct 3A. Two eyelets 2E which are attached to the faceplate 2F are also shown in FIG. 1 on the left. These eyelets can be used to fasten the washable pouch more securely to the user's abdomen using a rubber belt.

Figure 2:
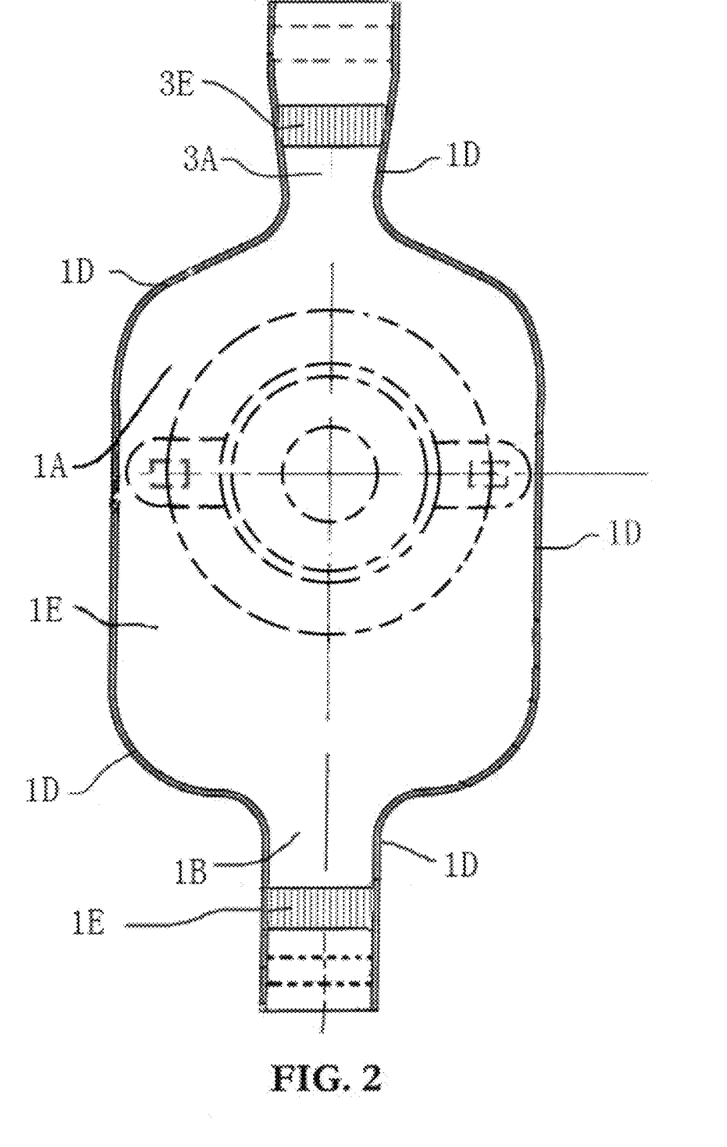
FIG. 2 depicts the front view of the washable pouch, which includes the frontal flexible wall 1E. The washing duct 3A and the draining duct 1B are also displayed.

FIG. 2 illustrates the front view of an embodiment of the washable pouch 1A. The front flexible wall 1E has two protruding ducts 3A and 1B i.e. the washing duct 3A and the draining duct 1B. The front flexible wall 1E is fused all along its perimeter 1D to the rear flexible wall 1F perimeter except for two short perimeter segments for the upper washing duct opening and the lower draining duct opening. The fusion strip 1D is shown as a wide dark line in FIG. 2. The washing duct 3A has a washing duct seal comprised of the interlocking type strip 3E which can be attached to a second interlocking type strip 3B (shown in FIG. 1) by folding the washing duct wall 3A. Folding the washing duct wall 3A seals the washing duct. This enables to block all flow through the washing duct when the washing duct seal is sealed. Similarly, the draining duct 1B has a draining duct seal comprised of the interlocking type strip 1E which can be attached to a second interlocking type strip 1C (shown in FIG. 1) by folding the draining duct wall 1B. Folding the draining duct wall 1B seals the draining duct. This enables to block all flow through the draining duct 1B when the draining outlet seal of 1B is sealed. The illustrations in FIG. 1 and FIG. 2 show the washing duct 3A and the draining duct 1B with unfolded—open seals.

Figure 3:
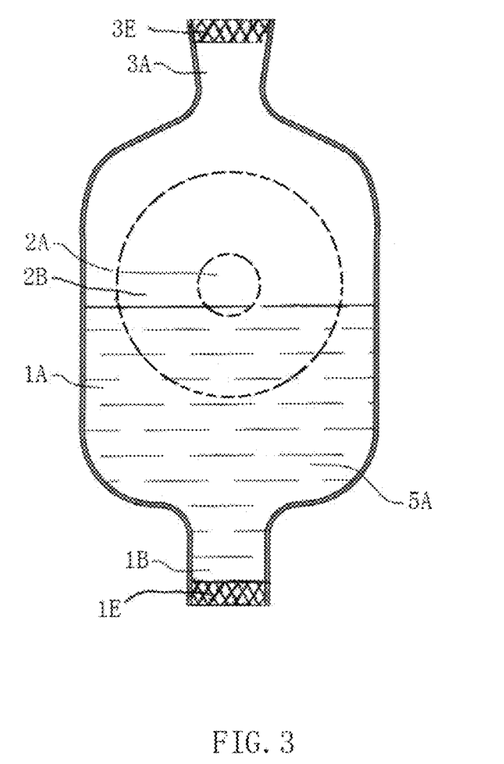
FIGS. 3 to 7 illustrate a frontal view of an embodiment of the washable pouch, describing a proposed washing and draining procedure of the pouch.

FIGS. 3-7 describe a proposed draining and washing procedure using the washable pouch 1A. In order to illustrate the different states of contents accumulated in the washable pouch during washing and draining, FIGS. 3-7 show the washable pouch as if it has a transparent frontal wall 1E. FIG. 3 describes the washable pouch 1A in the accumulation phase when both the draining duct 1B and the washing duct 3A are sealed and the discharged waste 5A which is excreted from the user's stoma via the abdominal inlet 2A is accumulated in the washable pouch 1A.

Figure 4:
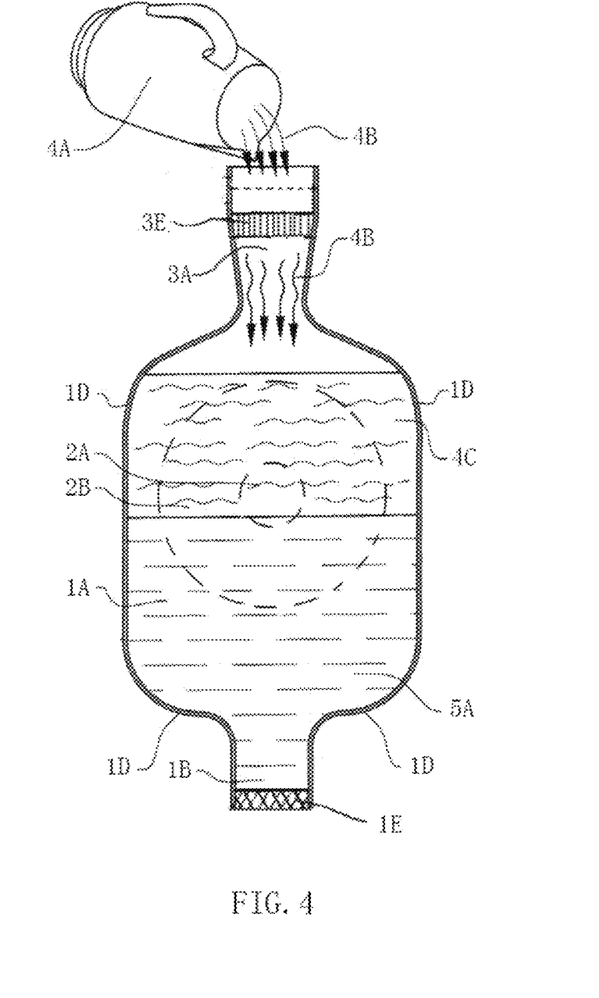

When the user decides to drain the washable pouch 1A, the user opens the washing duct seal 3B-3E of the washing duct 3A and pours water 4B into the washing duct 3A from the pitcher 4A. This step is illustrated in FIG. 4. The amount of water 4C in the washable pouch, which is poured from the pitcher 4A should be sufficient to create a fluent mixture with the accumulated discharged waste 5A in the pouch 1A. In our experience, the amount of water needed is about one glass. The draining duct seal 1C of the draining duct 1B is sealed during this phase.

Figure 5:
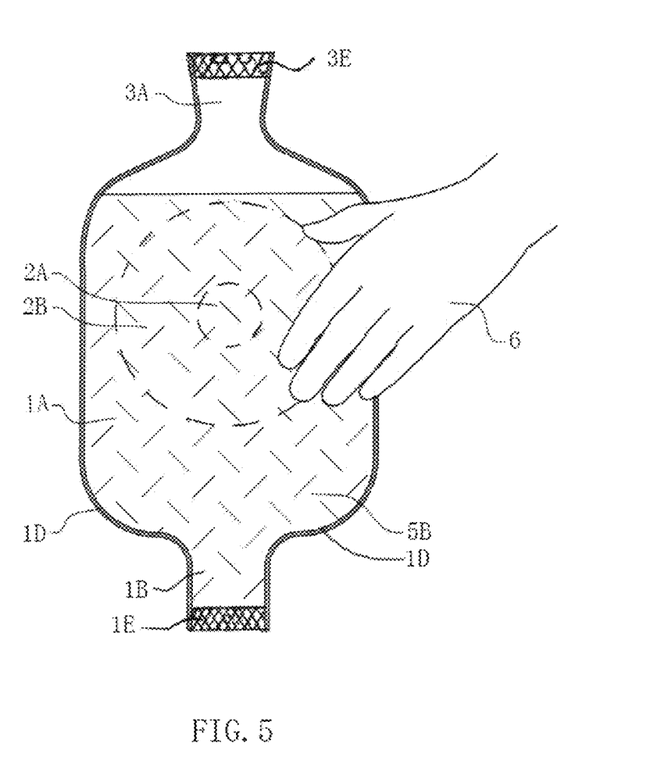

As illustrated in FIG. 5, the user then seals the washing duct 3A and squeezes the washable pouch 1A with the user's hands 6 several times until the water mixes with the discharged waste and creates a fluent mixture 5B. The squeezing and mixing step is described in FIG. 5. Both the draining duct seal of the draining duct 1B and the washing duct seal of the washing duct 3A remain closed during the mixing phase.

Figure 6:
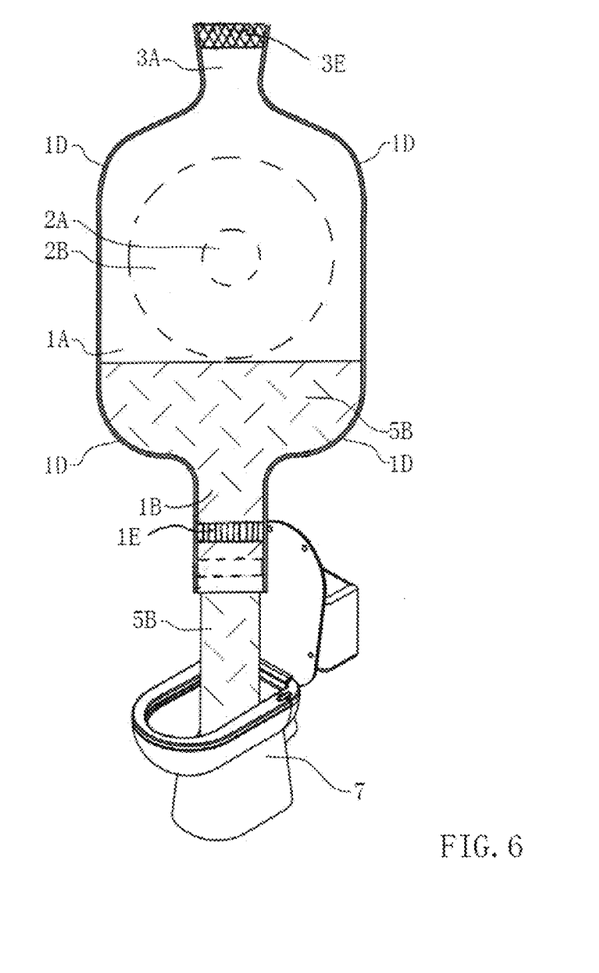
Figure 7:
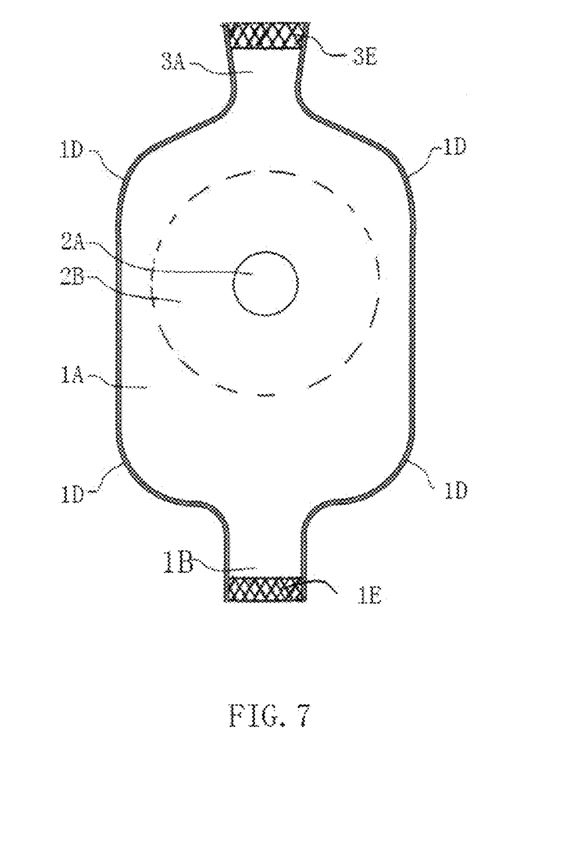

In FIG. 6, the user opens the draining duct 1B by separating and unfolding the sealing strips 1C-1E. Next, the user drains the mixture 5B into the toilet bowl 7. The washing duct seal 3B-3E remains closed at this phase. FIG. 7 describes the state of the washable pouch 1A after drainage is completed. The draining duct 1B and the washing duct 3A are sealed by folding the seals 1C-1E and 3B-3E respectively. At this stage the washable pouch is ready for the next discharged waste accumulation.

In our experience, almost all the discharged waste mixture 5B is drained at the first washing. If some discharged waste still remains in the washable pouch 1A, the user can repeat the washing procedure until the pouch is completely emptied. The user does not need to detach the washable pouch from the stoma at any time during the washing procedure.

What is claimed is:

1. A washable ostomy appliance configured to attach to a user in order to accumulate discharged waste and to be washed and drained without being detached from said user; the washable ostomy appliance comprising:

a washable pouch comprising:
        a central cavity,
        a front wall,
        a rear wall,
        an abdominal inlet opening,
        an abdominal inlet coupling,
        a draining outlet below and fluidly connected with said central cavity,
        a washing inlet above and fluidly connected with said central cavity;
        a washing duct and
        a draining duct;
        said washing duct comprising: a washing duct wall,
        a lower washing duct opening situated at a lower end of the washing duct,
        a washing duct seal situated at a top of the washing duct and
        an upper washing duct opening situated at an upper end of the washing duct seal;
        wherein said lower washing duct opening is attached to and fluidly connected with said washing inlet;
        said draining duct comprising: a draining duct wall,
        an upper draining duct opening situated at an upper end of the draining duct,
        a draining duct seal situated at a bottom of said draining duct and
        a lower draining duct opening situated at a lower end of said draining duct seal;
        wherein said upper draining duct opening is attached to and fluidly connected with said draining outlet;
    wherein said central cavity is fluidly connected to: said abdominal inlet opening, to said lower washing duct opening via said washing inlet and to said upper draining duct opening via said draining outlet;
    wherein the central cavity is situated between said front wall and said rear wall;
    wherein said abdominal inlet opening is situated in said rear wall;
    wherein said front wall and said rear wall are made of planar sheets made of flexible material;
    wherein said front wall and said rear wall are fused together at their perimeters except for a lower perimeter segment configured for the lower draining duct opening and an upper perimeter segment configured for the upper washing duct opening;
    wherein said abdominal inlet coupling comprises: an abdominal adhesive faceplate and an adhesive layer of a skin barrier surrounding a central opening of the abdominal adhesive faceplate; wherein said abdominal inlet opening is fluidly connected to said central opening;
    said abdominal adhesive faceplate comprising: a distal side and a proximal side; wherein said distal side is attached to said rear wall; said proximal side comprises said adhesive layer of the skin barrier surrounding said central opening; wherein said adhesive layer of the skin barrier is configured to adhere said abdominal adhesive faceplate to said user's abdominal skin surrounding said user's stoma.

2. The washable ostomy appliance of claim 1, wherein said proximal side further comprises a circular flexible adhesive strip, which surrounds and also is attached to said abdominal adhesive faceplate; whereby, said circular flexible adhesive strip is configured to adhere to said user's abdominal skin surrounding said adhesive layer of the skin barrier.

3. The washable ostomy appliance of claim 1, wherein said adhesive layer of the skin barrier has a tapered perimeter that is configured to reduce irritation of said user's abdominal skin when applied thereto.

4. The washable ostomy appliance of claim 1, wherein said abdominal inlet coupling has at least one eyelet which is configured to facilitate fastening said washable ostomy appliance to said user's body.

5. The washable ostomy appliance of claim 1, wherein an air filter is installed in an opening in said washing duct arterial wall.

6. The washable ostomy appliance of claim 1, wherein the washing duct wall has the shape of a funnel, wherein said upper washing duct opening of said washing duct wall is configured to be wider than said lower washing duct opening in both: (i) an open position when the washing duct seal is open; and (ii) a closed position when the washing duct seal is closed, such that the washing duct wall is configured to facilitate pouring of water into the upper washing duct opening when the upper washing duct opening is in said open position.

7. The washable ostomy appliance of claim 1, wherein the draining duct seal comprises a first multiplicity of interlocking strips that are configured to seal the lower draining duct opening by folding the draining duct wall such that the first multiplicity of interlocking strips are adhered to each other to seal the lower draining duct opening; and wherein the washing duct seal comprises a second multiplicity of interlocking strips that are configured to seal the upper washing duct opening by folding said washing duct wall such that the second multiplicity of interlocking strips are adhered to each other to seal the upper washing duct opening.

8. The washable ostomy appliance of claim 1, wherein said draining duct seal comprises a first multiplicity of joining strips and a first multiplicity of non-resilient bars that are configured to seal said lower draining duct opening by folding the draining duct wall and securing said first multiplicity of joining strips to each other using said first multiplicity of non-resilient bars;

said washing duct seal comprises a second multiplicity of joining strips and a second multiplicity of non-resilient bars that are configured to seal said upper washing duct opening by folding the washing duct wall and securing said second multiplicity of joining strips to each other using said second multiplicity non-resilient bars.

9. The washable ostomy appliance of claim 1, wherein said proximal side of said abdominal adhesive faceplate and said adhesive layer of said skin barrier have a convex shape.

* * * * *